(12) United States Patent
Datta et al.

(10) Patent No.: US 11,123,273 B1
(45) Date of Patent: *Sep. 21, 2021

(54) METHOD FOR PROVIDING BACTERICIDAL AND BACTERIOSTATIC ACTIVITY WITH A BIOSOLVENT FORMULATION

(71) Applicant: Vertec BioSolvents, Inc., Downers Grove, IL (US)

(72) Inventors: Rathin Datta, Chicago, IL (US); George Dymond Laubach, Elgin, IL (US); James E. Opre, Downers Grove, IL (US)

(73) Assignee: VERTEC BIOSOLVENTS, INC., West Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/939,854

(22) Filed: Jul. 27, 2020

(51) Int. Cl.
| | | |
|---|---|---|
| *A61K 8/37* | (2006.01) | |
| *A61K 8/34* | (2006.01) | |
| *A61Q 19/10* | (2006.01) | |
| *A61K 8/73* | (2006.01) | |
| *A61K 8/67* | (2006.01) | |

(52) U.S. Cl.
CPC ............... *A61K 8/37* (2013.01); *A61K 8/34* (2013.01); *A61K 8/345* (2013.01); *A61K 8/678* (2013.01); *A61K 8/731* (2013.01); *A61Q 19/10* (2013.01)

(58) Field of Classification Search
CPC . A61K 8/37; A61K 8/34; A61K 8/345; A61K 8/678; A61K 8/731; A61Q 19/10
See application file for complete search history.

(56) References Cited

U.S. PATENT DOCUMENTS

| | | | |
|---|---|---|---|
| 6,172,029 B1 * | 1/2001 | Mizutani | A01N 33/24 510/383 |
| 9,963,660 B2 | 5/2018 | Datta et al. | |
| 10,085,452 B2 | 10/2018 | Benkovic et al. | |
| 2005/0019355 A1 * | 1/2005 | Denton | A61K 8/37 424/401 |
| 2012/0148716 A1 * | 6/2012 | Doyle | A01N 37/42 426/310 |
| 2016/0304814 A1 * | 10/2016 | Datta | C11D 7/266 |

FOREIGN PATENT DOCUMENTS

WO   WO 2013/050591 A2   4/2013

OTHER PUBLICATIONS

Use of Benzyl Alcohol as a shipping and Storage Solution for Chromatography Media, GE Healthcare and Life Sciences, Application Note 28-9899-01AB, General Electric Company bulletin, (2012); 4 pages.

Barker, C. and S.F. Park, Sensitization of Listeria monocytogenes to Low pH, Organic Acids and Osmotic Stress by Ethanol, Applied and Environmental Microbiology, vol. 67 #4, 1594-2000, 2001, 17 pages.

Oh, D-H and D.L.Marshall, Antimicrobial activity of Ethanol, Glycerol Monolaurate or Lactic Acid Against Listeria monocytogenes, International Journal of Food Microbiology, 20, 239-246, 1993, 1 page, (Abstract Only).

* cited by examiner

*Primary Examiner* — Genevieve S Alley
(74) *Attorney, Agent, or Firm* — McCracken & Gillen LLC

(57) ABSTRACT

A biosolvent for cleansing surface that provides bactericidal and bacteriostatic activity such that the bacteriostatic activity continues to inhibit bacterial growth on the surface even after rinsing. The biosolvent comprises C2 to C4 alcohols and lactate esters of C2 to C4 alcohols. The bactericidal and bacteriostatic activity are especially useful for cleaning active biological surfaces and in particular for sanitizing hands.

12 Claims, 4 Drawing Sheets

METHOD FOR PROVIDING BACTERICIDAL AND BACTERIOSTATIC ACTIVITY WITH A BIOSOLVENT FORMULATION

INTRODUCTION/BACKGROUND

There are numerous cleaning formulations that are used to clean and disinfect a variety of surfaces. Only a few are recognized to provide bactericidal activity i.e. ability to kill many species of bacteria within a limited contact time (see references 1-4) Some examples are: hydrogen peroxide, chlorine, ethanol (at concentrations ~65%).

Alcohols are known to have bacteriostatic properties. Ion exchange resins, ultrafiltration membranes and other biosensitive processing agents are often kept in aqueous alcohol solutions for bacteriostatic preservations [see Handbook of Disinfectants and Antiseptics, J. M. Ascenzi ed., Marcel Dekker, Inc, New York (1996); "Use of Benzyl Alcohol as a shipping and Storage Solution for Chromatography Media", GE Healthcare and Life Sciences, Application Note 28-9899-01AB, General Electric Company bulletin, (2012); Barker et al., Appl Environ Microb, 67(4):1594-2000 (2001); and Oh et al., Int J Food Microbiol, 20:239-246 (1993)]. Organic acids such as formic, acetic, and lactic are also known to have bacteriostatic properties [See "Use of Benzyl Alcohol as a shipping and Storage Solution for Chromatography Media", GE Healthcare and Life Sciences, Application Note 28-9899-01AB, General Electric Company bulletin, (2012); Barker et al., Appl Environ Microb, 67(4):1594-2000 (2001); and Oh et al., Int J Food Microbiol, 20:239-246 (1993)].

However after their use, the activity of these formulations goes away because they are unstable, (e.g. peroxide, chlorine), they evaporate (e.g. ethanol), get diluted, or get washed away. None of such formulations provide long term bacteriostatic activity i.e. they cannot prevent the growth of bacteria after dilution with water, which invariably occurs after the cleaning action is over.

U.S. Pat. No. 9,963,660, discloses using a combination of ethanol and a lactate ester to dissolve food or bioprocess derived contaminants such as carbohydrates, proteins and fats from surfaces in the presence of water and provide bacteriostatic activity for a period of time even after water dilution. The individual solvents did not provide these enhanced activities. Moreover the '660 patent makes no suggestion that surfaces contacted with such solvent mixtures will provide bactericidal activity on microbially contaminated surfaces and also retain extended bacteriostatic properties especially with water dilution.

Prior work, such as U.S. Pat. No. 9,963,660, was focused on cleaning processing equipment, particularly for food production and machinery, such prior work does not remotely suggest that such solvent mixtures in their cleaning and removing of debris from equipment and machinery could work on active biological surfaces and not only remove and clean the debris but also provide very high bactericidal activity, and, most importantly, a bacteriostatic activity that remains even after dilution with water. In addition, such prior work as the '660 patent, make no suggestion that surfaces contacted with such solvent mixtures will retain extended bacteriostatic properties especially with the dilution of water. The '660 patent further recites that its "bacteriostatic activity is maintained in the used cleaning solution after rinsing and further dilution with water." Thus, the '660 patent relies on the presence of the used cleaning fluid for continued/residual bacteriostatic properties.

SUMMARY OF THE INVENTION

What has been discovered is a biosolvent formulation, comprising a C2 to C4 alcohol such as ethanol and a lactate ester of a C2 to C4 alcohol, such as ethyl lactate, that can sanitize surfaces contaminated with microbial contaminants such that while also providing very high bactericidal activity and also bacteriostatic activity that remains even after dilution with water. Microbially contaminated surfaces are surfaces that have microorganisms, namely bacteria but also yeast, fungi, and viruses. These microorganisms can be on layers either as single species or more often in multi species clusters.

In a particularly useful form this invention is the discovery of a method that uses a biosolvent mixture containing one or more C2 to C4 alcohols and a lactate ester of one or more C2 to C4 alcohols that is applied to surfaces having biological activity to kill and prevent the regrowth of bacterial contaminants. The mixture will sanitize active biological surfaces contaminated with microbial contaminants and provide very high bactericidal activity and also bacteriostatic activity even after dilution with water.

Accordingly, in one aspect this invention is a method for sanitizing a surface from microbial contamination with a biosolvent mixture that provides bactericidal activity and also provides bacteriostatic activity. The bacteriostatic activity remains and continues to prevent or inhibit microbial contamination even after contact with the surface. This aspect of the method can include contacting a surface containing microbial contamination with a biosolvent mixture comprising at least 60 wt. % of at least one C2 to C4 alcohol, at least 10 wt. % of at least one lactate ester of a C2 to C4 alcohol.

In a further aspect of sanitizing a surface the method includes maintaining aqueous conditions on the surface while contacting the surface with a biosolvent mixture to produce a surface mixture comprising the biosolvent mixture and water. A dilution ratio of no more than one-part biosolvent mixture to no greater than 10 parts of water is maintained on the surface. Contact of the surface with the biosolvent mixture provides a surface in a sanitized condition in which at least 99.99% of the microbial contamination is removed and the surface inhibits microbial contamination.

In other aspects of the invention aqueous conditions are maintained on the surface to produce a dilution ratio on a weight basis of one-part biosolvent mixture to no greater than five-parts water or one-part biosolvent mixture to no greater than three-parts water.

Surfaces for treatment by this invention include biologically active surfaces such as human skin. A particularly useful aspect of this invention is the contact of a person's hands with the biosolvent mixture.

In another aspect of the invention the ester is ethyl lactate and the alcohol is ethanol. Preferred compositions of the biosolvent mixture include on a w/w % basis 70 to 80% ethanol and 15 to 25% ethyl lactate. Such preferred mixtures may also contain from 3 to 5 wt. % glycerol.

Other aspects of this invention incorporate additives into the biosolvent mixture. Such additives include viscosifiers, particularly cellulose esters, fragrances, and organic acids such as acetic or lactic acid in a typical amount of 1 to 2 wt. %.

Sanitizing of active biological surfaces is a more specific aspect of the method of this invention. In this aspect the method sanitizes an active biological surface with a biosolvent mixture that provides bactericidal activity and also provides bacteriostatic activity wherein the bacteriostatic activity continues to inhibit microbial contamination even when the biosolvent mixture is in the presence of water. The method comprises sanitizing the active biological surface containing microbial contamination by contacting the active biological surface with a biosolvent mixture. The biosolvent mixture comprises at least 60 wt. % of at least one C2 to C4 alcohol and at least 10 wt. % of at least one lactate ester of a C2 to C4 alcohol and produces a cleansed condition on the active biological surface that inhibits microbial contamination. Sanitizing according to this aspect preferably produces an active biological surface with a bactericidal activity of at least 99.99%

In another aspect of sanitizing active biological surfaces, the method includes maintaining aqueous conditions on the active biological surface while contacting the active biological surface with the biosolvent mixture. The aqueous condition together with the biosolvent mixture produce a sanitizing mixture on the active biological surface comprising the biosolvent mixture and water in a range of between one-part biosolvent mixture to at least up to one-part water and up to one-part biosolvent mixture to not greater than ten-parts water on the active biological surface. In another aspect of the invention the resulting sanitizing mixture remains in contact with the active biological surface for at least 10 seconds and preferably for at least 20 seconds. An especially suitable active biological surface is a person's hands and the biosolvent mixture mixes with water expelled from the skin without the addition of external water.

Thus, in another aspect the invention is a method for sanitizing hands to remove microbial contamination with a biosolvent mixture that provides bactericidal activity and also provides bacteriostatic activity wherein the bacteriostatic activity continues to inhibit microbial contamination when diluted with water. In this aspect the method is used to sanitize a person's hands by contact with a biosolvent mixture comprising at least 60 wt. % of at least one C2 to C4 alcohol and at least 10 wt. % of at least one lactate ester of a C2 to C4 alcohol. Aqueous conditions are maintained while contacting the hands with the biosolvent mixture to produce a sanitizing mixture on the hands that comprises the biosolvent mixture and water. Contact with the sanitizing mixture sanitizes the hands and establishes a cleansed condition thereon that inhibits microbial contamination. In this aspect the aqueous conditions may be maintained to keep the sanitizing mixture at a dilution ratio not exceeding (wt./wt.) one-part biosolvent mixture to ten-parts water. Preferably the biosolvent mixture comprises on a weight basis 70 to 80% ethanol and 15 to 25% ethyl lactate. The biosolvent mixture may also comprise a total of 1% to 5% (w/w) of at least one of Vitamin E and a fragrance.

Accordingly, a representative the biosolvent mixture contains at least one C2 to C4 alcohol and at least one lactate ester of a C2 to C4 alcohol. The preferred mixture contains ethanol and ethyl lactate. The concentration range of the lactate ester can vary from about 10% to 40% (w/w) (and preferably between 15 to 25% w/w) with the remainder of the biosolvent mixture comprising the C2 to C4 alcohol and, if desired, additional additives. When present the additives typically have a concentration of less than 10 wt. % and more typically less than 5 wt. %.

In another preferred form, the alcohol content varies from 60% to 90% by weight and the lactate ester concentration is at least 10 wt. %.

DETAILED DESCRIPTION OF THE INVENTION

Figure 1:
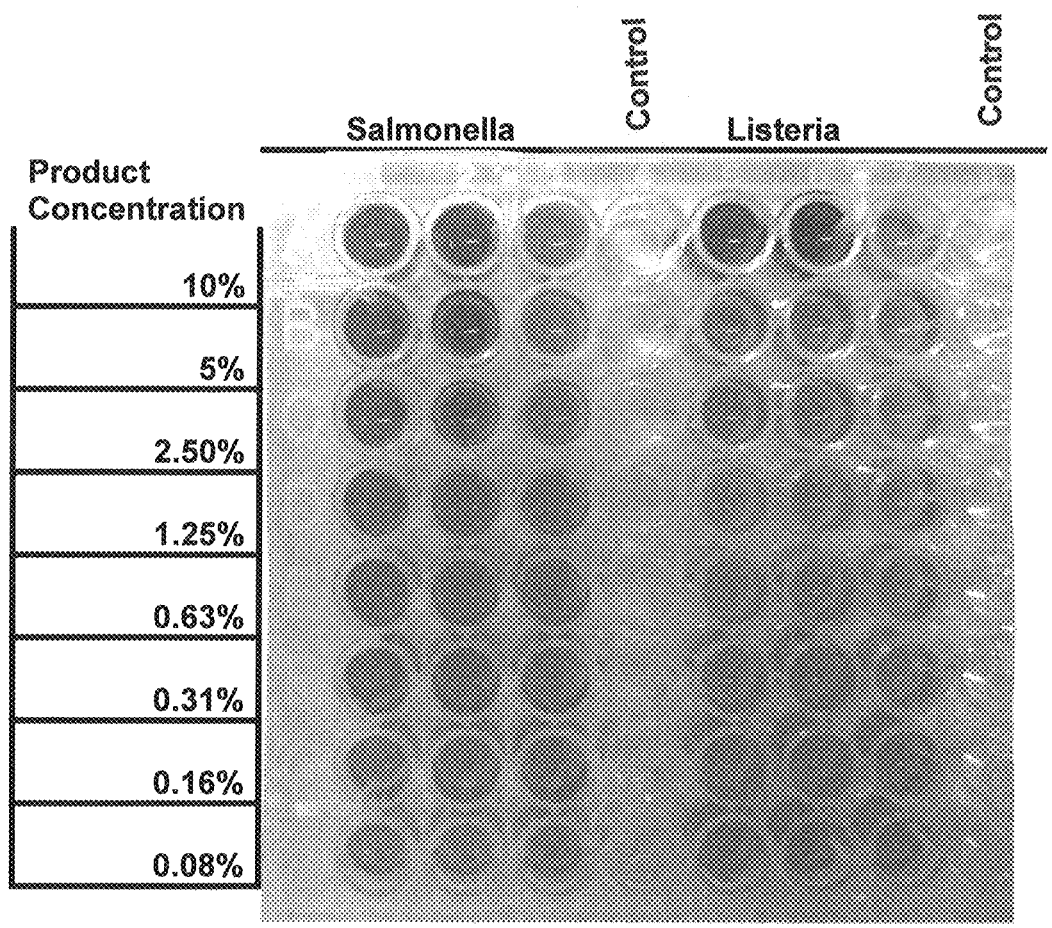
FIGS. 1-4 are photographs of a microtiter plates with sample wells that indicate bacteria concentrations and activity by the color of the sample in the well.

Biosolvents of this invention uniquely provides a chemistry that yields the properties to remove microbial contamination and inhibit the regrowth of such contamination even when diluted with water. The biosolvents highly oxygenated, hydrophilic composition containing bridging groups such as the alpha hydroxyl group of lactate enable its surface cleaning or cleansing action that removes microbial contamination from a surface and its sanitizing properties. Furthermore, these are small molecules that freely diffuse into layers and pores on both inanimate and biologically active surfaces. Thus, the small molecules of the biosolvent mixture can readily reach the target area for removal of the microbial contaminants providing cleansing action as well as bactericidal and bacteriostatic activity by simple flow and molecular diffusion. Again, the bacteriostatic activity will remain even after dilution of the biosolvent. The present invention can also leave a residue on surfaces, particularly biologically active surfaces present that prolongs the bacteriostatic properties of the biosolvent.

Accordingly, the biosolvent mixture of this invention can sanitize a wide range of surfaces. The surfaces can be inanimate such as metal, plastics, ceramics, furniture wood and the like. Surfaces can be biologically active such as skin and other exposed tissues such as gums, teeth, nails and such, of live animals and humans.

In addition, the water miscibility of the biosolvent readily combines it with the water present in or on the active biological surfaces (such as the skin) and the mixture can remain there for long periods of time while still providing bacteriostatic activity. The water allows the lactate ester to hydrolyze and provide, ethanol, lactic acid and/or lactate salt which are all known to be good for the skin. This hydrolysis can slowly lower the pH value. When it occurs, the resulting production of added ethanol, lactic acid and the pH drop increases the bacteriostatic activity of the biosolvent mixture in the sanitization method.

Water or moisture of some kind is typically present or provided when the biosolvent mixture contacts a surface for sanitizing. In such sanitizing methods the biosolvent mixture is maintained under aqueous conditions. Maintaining the surface under aqueous conditions means keeping water present either by extrinsic addition or, particularly in the case of active biological surfaces, the surface may have intrinsic water present. For example, human skin is an active biological surface that provides intrinsic water particularly through the palms of the hands. The eccrine sweat glands in active sweating provide moisture on the palms or transdermal water loss can provide gaseous water.

Thus, a major application of this invention is the sanitization of skin surfaces such as a hands with the biosolvent mixture in the form of a hand sanitizer. The biosolvent mixture, hand-sanitizer very effectively removes contaminants, particularly microorganisms from the hands. The application method can comprise the simple contact of one or both hands with the biosolvent mixture in a similar or same manner of use as other hand sanitizers where after application the hand sanitizer remains on the skin without rinsing. In the case of ordinary hand washing, the biosolvent mixture provides a superior sanitizing medium. Whether washing hands with water and the biosolvent mixture or applying the biosolvent mixture to hands without extrinsic water, application of the biosolvent continues to provide the skin with bacteriostatic activity.

More complex formulations of the biosolvent mixture can include a variety of additives and modifiers such as viscosifiers, fragrances, glycerol, and surfactants. Viscosifiers, such as cellulose esters will thicken the biosolvent mixture to facilitate its application to many surfaces.

Many of the other additives and modifiers adapt the biosolvent mixture for application to skin. Adding fragrance(s) can make the biosolvent mixture more pleasing to use on the skin. With the addition of glycerol, the biosolvent can have moisturizing activity. Adding nutrients such as Vitamin E can give the biosolvent the ability nurture and promote skin healing and health.

A typical composition of the biosolvent formulation (w/w %) is: ethanol (~75%), Ethyl lactate (~20%), and glycerol (~4%). Other minor components such as vitamin E, viscosifiers (typically cellulose ester), and fragrance(s) can constitute ~1%.

The biosolvent mixture may be formulated with denatured alcohol; a preferred denaturant is isopropanol. In the formulation anhydrous ethanol is preferred, but azeotrophic ethanol typically containing 5 w/w % water, may be used.

Surfactants for addition to the biosolvent include common anionic, cationic or neutral surfactants that are readily soluble in the various biosolvent mixtures. Suitable nonionic surfactants include linear long chain, e.g., $C_{10}$-$C_{18}$, alcohol ethoxylate ethers. Other surfactants include long chain alcohol ethoxylates of individual alcohols such as lauryl (C12), myristyl (C14), palmityl (C16) and stearyl (C18) alcohols. Other such surfactants include PEG-3 to PEG-11 cocamide. Ethoxylated nonylphenols are also useful such as nonoxynol-2 and nonoxynol-12. Similar ethoxylated octylphenols are commercially available for use, in particular, octoxynol-5 and octoxynol-8.

Useful anionic surfactants are preferably sulfonates, as carboxylates can build up on surfaces after several uses and sulfate esters can exhibit stability problems. Illustrative sulfonate surfactants include the long chain alkylbenzene sulfonates such as isopropylamine dodecylbenzene sulfonate. Other alkylbenzene sulfonate surfactants include sodium cetylbenzenesulfonate and disodium lauryl phenyl ether disulfonate. Still further sulfonates include the long chain alkane sulfonates such as the C13-C17 alkane and C14-C18 alkane sulfonates and the ethoxylated long chain alcohol sulfonates.

Suitable cationic surfactants are reaction products of long chain alkyl halide compounds with a trisubstituted amine to produce a long chain alkyl trisubstituted ammonium halide compound. Such compounds are illustrated by mono-long chain di-methyl or -diethyl benzyl ammonium salts, that are also useful herein. For example, mixed $C_{12}$-$C_{18}$ alkyl benzyl dimethyl or diethyl quaternary ammonium salts are also highly soluble in excess of 20% in the biosolvent mixtures. Another useful cationic surfactant is the reaction product of trimethylamine and cetyl bromide.

Small quantities of organic acids having readily solubility in the biosolvent mixtures can be added to the biosolvent mixture. Typical concentrations of such acids in the biosolvent mixture range from 1 to 2 wt. %. Preferred organic acids are acetic acid and lactic acid.

The following examples demonstrate the efficacy and benefits of the biosolvent mixture of this invention.

Example 1. Bactericidal Activity of Formulation

This discovery is supported by tests conducted by an independent microbiological testing laboratory using approved methods.

Bactericidal activity tests following the FDA guidelines (ref. 6) were conducted on 18 bacterial species after an exposure time of 20 seconds. The results show a 99.99% 'KILL' i.e. ability to kill bacteria within this limited contact time. The following description is summarized below.

Objective

To determine the antimicrobial efficacy of one test product when challenged against eighteen different microorganisms in an in-vitro time kill evaluation using a 20 seconds contact time.

Test Sample Description
1. A Biosolvent Test Formulation of this invention comprising approximately 75 wt. % ethanol and approximately 20 wt. % ethyl lactate was used in all tests. A similar biosolvent formulation is available commercially under the name Vertec Bio™ Sanitizer.

Test Organisms
1. *Staphylococcus aureus* ATCC #6538
2. *Staphylococcus epidermis* ATCC #12228
3. *Staphylococcus hominis* ATCC #700236
4. *Staphylococcus haemolyticus* ATCC #29970
5. *Micrococcus luteus* ATCC #7468*
   *ATCC #7468 is currently identified by ATCC as *Micrococcus yunnanensis*.
6. *Candida albicans* ATCC #10231
7. *Escherichia coli* ATCC #25922
8. *Pseudomonas aeruginosa* ATCC #15442
9. *Pseudomonas aeruginosa* ATCC #27853
10. *Proteus mirabilis* ATCC #7002
11. *Serratia marcescens* ATCC #14756
12. *Streptococcus pyogenes* ATCC #12344
13. *Enterococcus faecalis* ATCC #29212
14. *Enterococcus faecium* VRE ATCC #700221
15. *Streptococcus pneumoniae* ATCC #49150
16. *Haemophilus influenza* ATCC #19418
17. *Bacteroides fragilis* ATCC #25285
18. *Klebsiella pneumoniae* ATCC #4352

Test Protocol—Neutralization Validation

Summary—The purpose of a neutralization validation is to determine if the active ingredient in a product no longer has the ability to kill the test organism after the product is added to the neutralizer.

The product was added to D/E neutralizing broth at the same concentration as it would be added in the kill study, a 1:10 dilution. For the control, the product was also added to an aliquot of phosphate-buffered saline (PBS). This dilution of the product may also contribute to the neutralization. The *Staphylococcus aureus* ATCC #6538 and *Escherichia coli* ATCC #25922 were used as the challenge for this validation and applied at a final concentration of 30-100 CFU/mL, as per standard test method, ASTM E1054. A suspension was prepared by the following steps:
1. Add 1.0 mL of product with 9.0 mL of D/E broth
2. Mix 5 seconds
3. Add 0.1 mL of a $10^4$ CFU/mL bacterial suspension, resulting in a 1:100 dilution of the organism
4. Mix again, for a total of 20 seconds
5. Plate the resulting suspension by quantitative pour plates Test Protocol—Time Kill Study Summary—Overnight broth cultures of the organisms were adjusted spectrophotometrically to a $10^8$ CFU/mL concentration. These suspensions were used as the inoculum working suspension, added to the test product and mixed for 20 seconds. After the contact time, an aliquot of the dosed product was transferred to the D/E broth, mixed, serially diluted and plated. An initial serial dilution of each inoculum was performed to confirm the concentration of the challenges. The PBS control was also run at the contact time and served as the baseline for the reduction calculations and confirmation of the organism's viability during the challenge.

Inoculum Preparation:
6. All test organisms were inoculated into Tryptic Soy Broth (TSB) and shaken overnight at 35° C. except for the following organisms:
   a. *Streptococcus pyogenes* and the 2 *Enterococcus* strains were inoculated into Brain Heart Infusion (BHI) broth and shaken overnight at 35° C.
   b. *Bacteroides fragilis* was inoculated into BHI broth and incubated overnight in the anaerobic incubator.
   c. The *Haemophilus influenzae* was grown overnight on Chocolate Agar plates and transferred directly by swab to BHI broth.
   d. The *Streptococcus pneumoniae* was grown overnight on Blood Agar plates and transferred directly by swab to BHI broth.
7. Immediately prior to use, the overnight cultures were adjusted spectrophotometrically to a concentration of $10^8$ CFU/mL, plated quantitatively for confirmation of the concentration and used as the working inoculums.

Test Procedure:
8. Product was tested at 100% concentration.
9. The 9.9 mL of product was mixed with 0.1 mL of the working inoculum (a 1:100 dilution) in a sterile 50 mL centrifuge tube and mixed vigorously (final challenge concentration=$10^6$ CFU/mL)
10. A 1.0 mL aliquot of the inoculated mixture was dispensed into a sterile 9.0 mL tube of D/E neutralizing broth (a 1:10 dilution) at the 20 second contact time. The neutralizing broth was mixed well and quantitatively plated in duplicate to determine the number of surviving organisms after the contact time.
11. A PBS control was run to confirm the concentration of the inoculum for use in the calculations.
12. Standard Methods Agar was used for most bacterial pour plates. Molten Blood Agar (TSA with 5% sheep blood) was used for the *Enterococcus* and *Streptococcus* pour plates. Chocolate agar was used for *Haemophilus influenzae* spread plates. Blood Agar plates were used the *Bacteroides* spread plates. The detection limit on pour plates is 10 CFU/mL The detection limit on spread plates is 20 CFU/mL Calculations % Reduction in $CFU/mL = [(A-B)/A] \times 100$ $Log_{10}$ Reduction = $Log_{10}(A) - Log_{10}(B)$ Where:
A=average CFU/mL of the organism recovered from the PBS challenge after contact time
B=average CFU/mL of the organism recovered from the product challenge after contact time Neutralization Results
Analysis of biosolvent test formulation
against *S. aureus* ATCC# 6538

| Test Product | Recoverable CFU/mL in PBS | Recoverable CFU/mL in D/E broth |
|---|---|---|
| Biosolvent Test Formulation | $3.5 \times 10^2$ | $3.3 \times 10^2$ |

Initial concentration of *S. aureus* ATCC 6538 in the test above was $4.3 \times 10^4$ CFU/mL Analysis of product against *E. coli* ATCC# 25922

| Test Product | Recoverable CFU/mL in PBS Control | Recoverable CFU/mL in D/E broth |
|---|---|---|
| Biosolvent Test Formulation | $3.5 \times 10^2$ | $3.8 \times 10^2$ |

Initial concentration of *E. coli* ATCC 25922 in the test above was $4.2 \times 10^4$ CFU/mL.

Kill Study Results for: Biosolvent Test Formulation

| Challenge Organism | PBS Control 20 sec | Product 20 sec | Percent Reduction (%) | Log Reduction |
|---|---|---|---|---|
| *S. aureus* ATCC #6538 | $3.2 \times 10^6$ | $<1.0 \times 10^1$ | >99.9997 | >5.51 |
| *S. epidermidis* ATCC #12228 | $3.1 \times 10^6$ | $<1.0 \times 10^1$ | >99.9997 | >5.48 |
| *S. hominis* ATCC#700236 | $2.3 \times 10^6$ | $<1.0 \times 10^1$ | >99.9996 | >5.35 |
| *S. haemolyticus* ATCC#29970 | $2.5 \times 10^6$ | $<1.0 \times 10^1$ | >99.9996 | >5.39 |
| *M. luteus* ATCC#7468 | $6.9 \times 10^5$ | $<1.0 \times 10^1$ | >99.9985 | >4.84 |
| *C. albicans* ATCC#10231 | $2.3 \times 10^5$ | $<1.0 \times 10^1$ | >99.9957 | >4.36 |
| *E. coli* ATCC#25922 | $3.1 \times 10^6$ | $<1.0 \times 10^1$ | >99.9997 | >5.48 |
| *Ps. aeruginosa* ATCC#15442 | $2.6 \times 10^6$ | $<1.0 \times 10^1$ | >99.9996 | >5.41 |
| *Ps. aeruginosa* ATCC#27853 | $2.9 \times 10^6$ | $<1.0 \times 10^1$ | >99.9996 | >5.45 |
| *P. mirabilis* ATCC#7002 | $3.4 \times 10^6$ | $<1.0 \times 10^1$ | >99.9997 | >5.53 |
| *S. marcescens* ATCC# 14756 | $3.2 \times 10^6$ | $<1.0 \times 10^1$ | >99.9997 | >5.50 |
| *S. pyogenes* ATCC#12344 | $1.1 \times 10^6$ | $<1.0 \times 10^1$ | >99.9991 | >5.04 |
| *E. faecalis* ATCC#29212 | $3.4 \times 10^6$ | $<1.0 \times 10^1$ | >99.9997 | >5.53 |
| *E. faecium* ATCC# 700221 | $3.1 \times 10^6$ | $<1.0 \times 10^1$ | >99.9997 | >5.49 |
| *S. pneumoniae* ATCC# 49150 | $1.1 \times 10^6$ | $<1.0 \times 10^1$ | >99.9991 | >5.02 |
| *B. fragilis* ATCC#25285 | $9.7 \times 10^6$ | $<1.0 \times 10^1$ | >99.9998 | >5.99 |
| *H. influenza* ATCC# 19418 | $7.9 \times 10^6$ | $<2.0 \times 10^1$ | >99.9997 | >5.60 |
| *K. pneumoniae* ATCC# 4352 | $2.8 \times 10^6$ | $<1.0 \times 10^1$ | >99.9996 | >5.44 |

Hence, the biosolvent formulation of this invention has very high bactericidal activity of a minimum of 99.99%.

Example 2. Bacteriostatic Activity of the Formulation

In separate tests conducted by an independent certified microbial testing laboratory, another method called Microtox was used to evaluate bacteriostatic activity of a similar biosolvent formulation of ethanol and the lactate ester-ethyl lactate. Bacteriostatic activity was found against several species of food pathogenic bacteria as well as some others, even after 5-fold dilution with water.

Methods to determine minimum inhibitory concentrations of biocides or bacteriostatic agents that work in processing liquids to inhibit microbiological growth have been developed and optimized (ref. 7). Typically this involves (a) obtaining a known volume aliquot of the contaminated aqueous system; (b) adding thereto a known amount of an oxidation reduction indicator dye, which indicator dye is capable of reacting with dehydrogenase enzymes produced by said microbiological organisms; (c) adding thereto sufficient nutrients capable of accelerating microbiological organism activity, thereby forming a reaction product between reducing enzymes and the oxidation-reduction indicator dye; and then, (d) obtaining multiple aliquots of the indicator dye treated, nutrient treated, aqueous system and transferring each of said multiple aliquots to a microtitration plate containing multiple sample wells, each well containing but one of the multiple aliquots, and then; (e) adding to at least one column of these sample wells on said titration plate a serially diluted amount of at least one antimicrobial agent, provided that a single column is treated with only one said antimicrobial agent; and further provided that at least one column is left untreated; thereby forming the arrangement of sample wells on the treated titration plate; (t) and then incubating said treated titration plate at a temperature essentially equivalent to the temperature of the contaminated aqueous system from which the aliquot was originally taken for a period of time sufficient to develop the change in the indicator dye color by the reaction of the indicator dye with the reducing enzymes produced by nutrient acceleration of microbiological metabolism; and then (g) comparing the first change in color in dye relative to the untreated column to determine the minimum inhibitor concentration of the antimicrobial agent which inhibits growth of the microbiological organism contained in said contaminated aqueous system.

Such a method (ref. 7) is optimized under the Trademark of MiniTox™ and tests are routinely practiced and results provided by microbiological testing laboratories such as: The MicroStar Lab LTD located at 130 Erick Street in Crystal Lake, Ill. 60014.

A biosolvent formulation of 80% ethanol and 20% ethyl lactate was diluted fivefold with water as would typically be used during a sanitizing step—aka cleaning step, followed by dilution by the presence of water in the skin or during the rinsing process. This solution was kept as is and at room temperature; hydrolysis of the ester continued. This solution was serially diluted with broth and media components for the MiniTox tests in microtiter plates.

Two bacterial cultures *Salmonella choleraesuis* ATCC 10708 and *Listeria* Monocytogenis ATCC 19115 were used for the tests. Bacteria of the *Salmonella* species are known pathogens that contaminate meat and vegetable types of food and *Listeria* species are known to contaminate milk and related foods.

The results clearly show:

At a 5% concentration (i.e. 20× dilution) the biosolvent formulation controlled the growth of *Salmonella Choleraesuis* and 2.5% concentration (i.e. 40× dilution) slowed the growth rate.

At a 10% concentration (i.e. 10× dilution) the formulation controlled the growth of *Listeria* Monocytogenis and 5% concentration (i.e. 20× dilution) slowed the growth rate.

This is further shown in FIG. 1 that shows the photograph of the microtiter plates where a clear blue color indicate bacterial growth inhibition and bacteriostatic activity while a purple color indicates slowdown of growth and the red color shows no activity.

Example 3. Bacteriostatic Activity—Further Tests on 15 Bacterial Species

An additional fifteen species of bacteria from a wide genus range were tested using the modified MiniTox™ method. These organisms are found in many surfaces such as skin and other habitats and are in the recommended list of bacterial species under the FDA guidelines (ref. 6). The work was performed by a certified microbial testing laboratory and is summarized below.

Objective:

To determine the lowest concentration of Biosolvent Test Formulation that controls the growth of 15 microorganisms, as demonstrated in a modification of the MiniTox™ test.

Test Sample Identification:

Biosolvent Test Formulation—a biosolvent formulation of this invention.

Test Organisms:

1. *Staphylococcus aureus* ATCC #6538
2. *Staphylococcus epidermidis* ATCC #12228
3. *Staphylococcus hominis* ATCC #700236
4. *Staphylococcus haemolyticus* ATCC #29970
5. *Micrococcus luteus* ATCC #7468
6. *Escherichia coli* ATCC #25922
7. *Klebsiella pneumoniae* ATCC #4352
8. *Pseudomonas aeruginosa* ATCC #27853
9. *Proteus mirabilis* ATCC #7002
10. *Serratia marcescens* ATCC #14756
11. *Streptococcus pyogenes* ATCC #12344
12. *Enterococcus faecalis* ATCC #29212
13. *Enterococcus faecium* ATCC #700221
14. *Streptococcus pneumoniae* ATCC #49150
15. *Candida albicans* ATCC #10231

Test Set-Up:

The sanitizer was serially diluted down the columns in a sterile 96-well microtiter plate that contained 100 µl of phosphate-buffered saline (PBS) in all wells. Table 1 shows final concentrations of sanitizer ranged from 66% to 6%. No sanitizer was added to row 8, which served as the positive control.

TABLE 1

| Sanitizer Concentrations | |
|---|---|
| Row 1: 66% | Row 5: 13% |
| Row 2: 44% | Row 6: 9% |
| Row 3: 30% | Row 7: 6% |
| Row 4: 20% | Row 8: 0% (control) |

Overnight, shaken broth cultures of the test organisms were diluted to target concentrations of $10^8$ CFU/mL. For each test organism, a 10 µL aliquot was added to each well of 2 duplicate columns and mixed, effectively diluting the organism concentration to $10^7$ CFU/mL. After 2 minutes of contact time between the sanitizer and the test organism, 10 µL aliquots of a resazurin/nutrient solution were added to each well, providing nutrient for the surviving organisms. The plates were incubated until the control wells for each organism turned from purple to pink, and the well with the lowest concentration of diluted sanitizer biosolvent formulation that did not turn pink were recorded as the endpoint.

Figure 2:
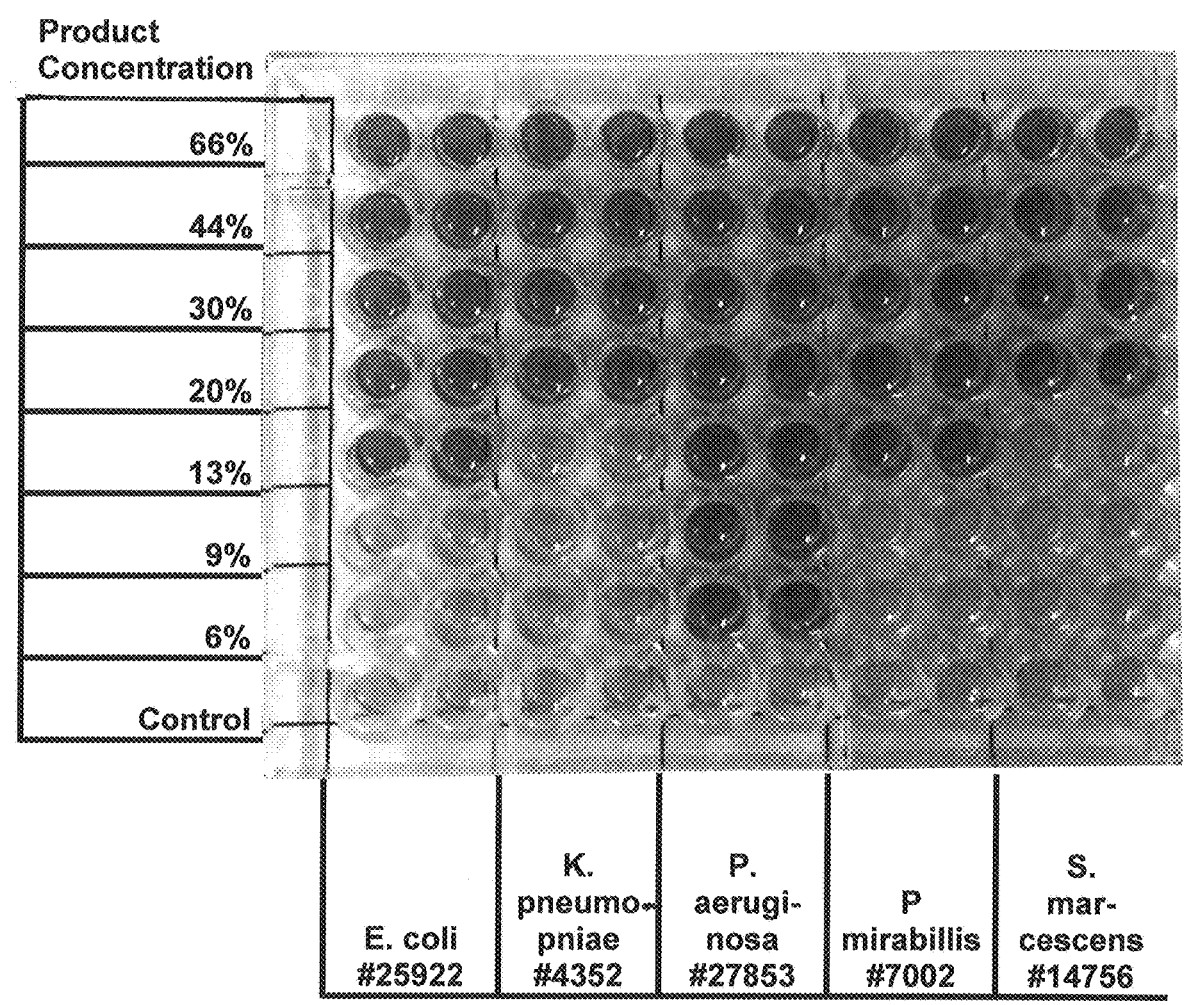
Figure 3:
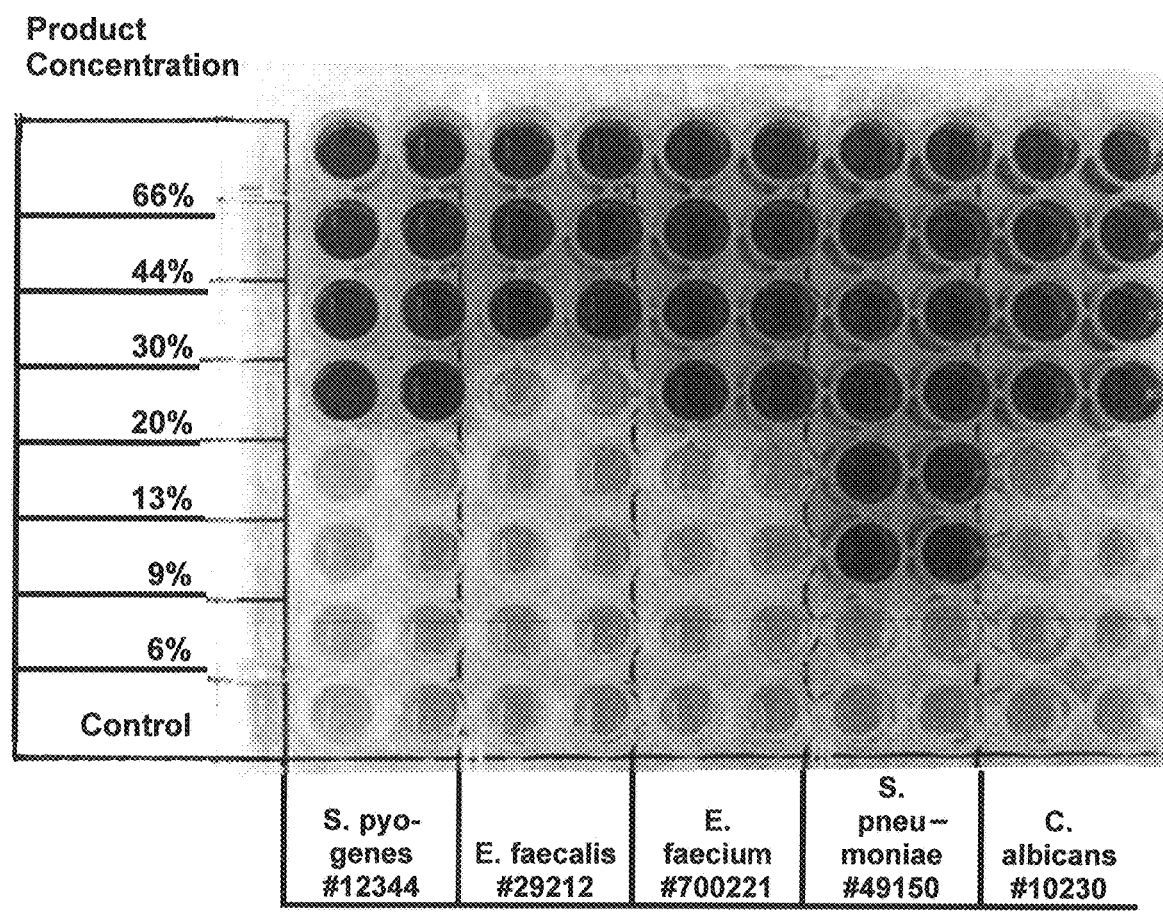
Figure 4:
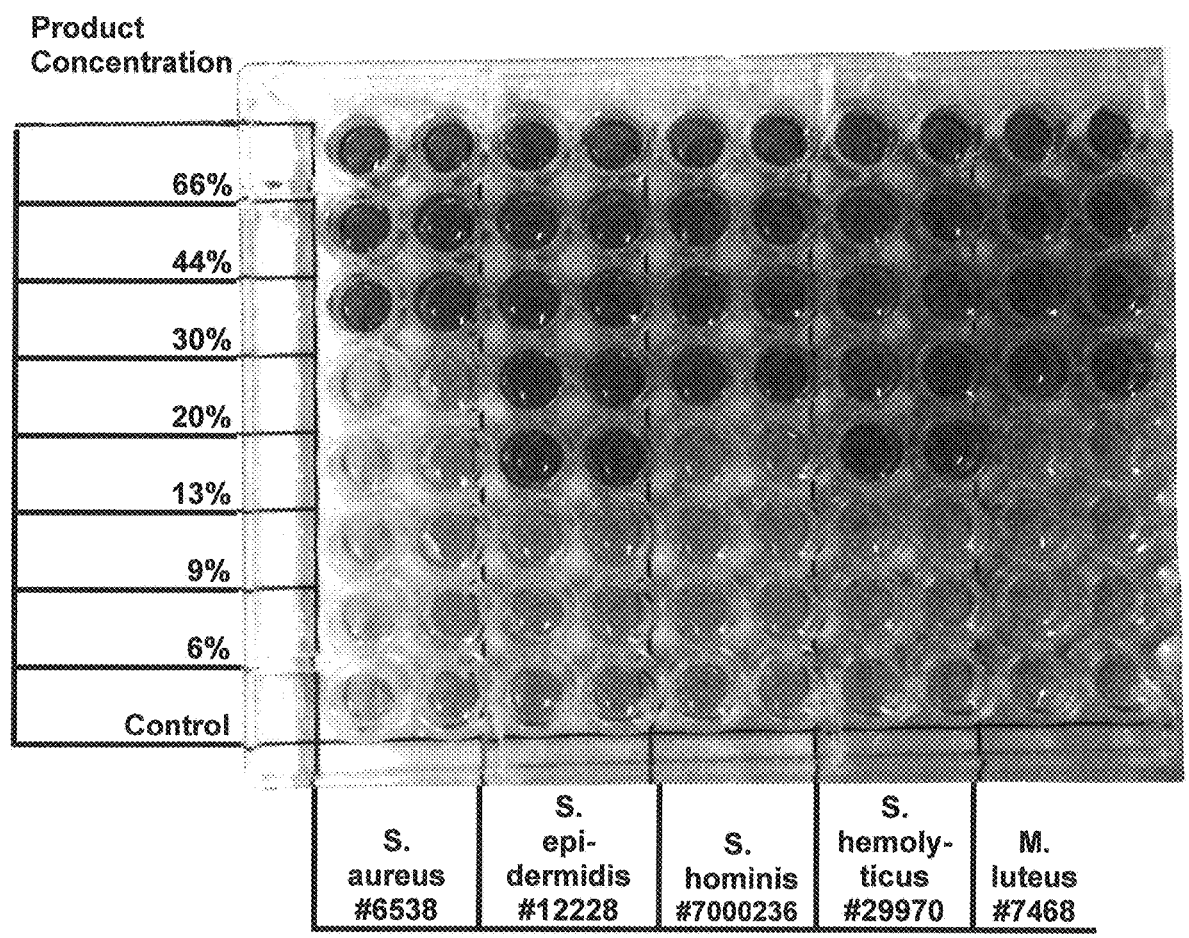

Test Results:

FIG. 2 shows a photo image of first test group of five bacterial species, FIG. 3 shows the image of the second group of five bacterial species, and FIG. 4 shows the image of the second group of five bacterial species.

Tables 2, 3 and 4 lists the initial inoculum concentration and the lowest effective sanitizer concentration for the test organisms.

TABLE 2

|  | Initial Inoculum Concentration (CFU/mL) | Lowest Effective Sanitizer Concentration |
|---|---|---|
| *Staphylococcus aureus* ATCC #6538 | $3.5 \times 10^8$ | 30% |
| *Staphylococcus epidermidis* ATCC #12228 | $2.7 \times 10^8$ | 13% |
| *Staphylococcus hominis* ATCC #700236 | $1.0 \times 10^8$ | 20% |
| *Staphylococcus haemolyticus* ATCC #29970 | $1.0 \times 10^8$ | 20% |
| *Micrococcus luteus* ATCC #7468 | $8.1 \times 10^8$ | 20% |

TABLE 3

|  | Initial Inoculum Concentration (CFU/mL) | Lowest Effective Sanitizer Concentration |
|---|---|---|
| *Escherichia coli* ATCC #25922 | $3.1 \times 10^8$ | 13% |
| *Klebsiella pneumoniae* ATCC #4352 | $3.8 \times 10^8$ | 20% |
| *Pseudomonas aeruginosa* ATCC #27853 | $1.4 \times 10^8$ | Less than 6% |
| *Proteus mirabilis* ATCC #7002 | $4.1 \times 10^8$ | 13% |
| *Serratia marcescens* ATCC #14756 | $1.4 \times 10^9$ | 20% |

TABLE 4

|  | Initial Inoculum Concentration (CFU/mL) | Lowest Effective Sanitizer Concentration |
|---|---|---|
| *Streptococcus pyogenes* ATCC #12344 | $9.4 \times 10^8$ | 20% |
| *Enterococcus faecalis* ATCC #29212 | $4.6 \times 10^8$ | 30% |
| *Enterococcus faecium* ATCC #700221 | $2.8 \times 10^8$ | 20% |
| *Streptococcus pneumoniae* ATCC #49150 | $1.2 \times 10^8$ | 9% |
| *Candida albicans* ATCC #10231 | $1.8 \times 10^7$ | 20% |

These results clearly show that the biosolvent formulation of the current invention provides bacteriostatic activity i.e. prevents growth of bacteria even after very substantial (3 fold to 14 fold) dilution with water.

Example 4. Handsanitizer Tests

A hand sanitizer batch using the formulation described earlier was prepared and samples were provided to more than one hundred test subjects who volunteered to test it and provide feedback comparing the previously described formulation to the existing sanitizers they commonly used. The test subjects did not wash their hands prior to testing the formulation. A significant result was that all of the test subjects experienced the feel of cleanliness of their hands from the application of the formula. The test subjects were asked specific questions that resulted in the ratings on a scale of 1 to 10 are summarized below:

1. Do you or other family members that tested the product, use hand sanitizers regularly?—Yes—
2. Hand feel. Please rate you response (1—no to 10—excellent) scale.

| 2a. Hand feel after application. | 10 | — |
| 2b. Drying time and feel after drying. | 10 | — |
| 2c. Feel of "cleanliness" after use. | 10 | — |

3. Our product has some properties that are different from Hand Sanitizers that are typically available. These properties are based on our recent discoveries. Please rate your response (1—no to 10—excellent) scale.

| 3a. The biocidal activity lasts longer. | 10 | — |

The results of these tests show a very high desirability and utilitarian value. Thus, this invention is validated by extensive microbiological test results and feedback from users of the formulated biosolvent mixture.

REFERENCES

1. Handbook of Disinfectants and Antiseptics, Joseph M. Ascenzi editor, Marcel Dekker, Inc, New York. 1996.
2. Use of Benzyl Alcohol as a shipping and Storage Solution for Chromatography Media, GE Healthcare and Life Sciences, Application Note 28-9899-01AB, General Electric Company bulletin, 2012.
3. Barker, C. and S. F. Park, Sensitization of *Listeria monocytogenes* to Low pH, Organic Acids and Osmotic Stress by Ethanol, Applied and Environmental Microbiology, vol. 67 #4, 1594-2000, 2001.
4. Oh, D-H and D. L. Marshall, Antimicrobial activity of Ethanol, Glycerol Monolaurate or Lactic Acid Against *Listeria monocytogenes*, International Journal of Food Microbiology, 20, 239-246, 1993.
5. U.S. Pat. No. 9,963,660. Method of Cleaning with Enhanced Bacteriostatic Action Using a Composition of Alcohol and Lactate Esters, Rathin Datta and George Laubach, May 8, 2018.
6. FDA guideline. FEDERAL Register/Vol. 81 No. 126/Jun. 30, 2016/Proposed Rules.
7. U.S. Pat. No. 5,206,151. Rapid Selection of Biocide Using a Reduction Oxidation Indicator System, Linda R. Robertson, Apr. 27, 1993.

The invention claimed is:

1. A method for sanitizing human skin with a biosolvent mixture that provides bactericidal activity and also provides bacteriostatic activity wherein the bacteriostatic activity remains when the biosolvent mixture is in the presence of water, the method comprising: contacting the human skin with a biosolvent mixture comprising at least 60 wt. % of at least one $C_2$ to $C_4$ alcohol and at least 10 wt. % of at least one lactate ester of a $C_2$ to $C_4$ alcohol and without the addition of extrinsic water at the time of contacting to kill bacterial contaminants and to leave a residue of the biosolvent mixture on the human skin and to produce a cleansed condition that continues to provide the bacteriostatic activity.

2. The method of claim 1 wherein the human skin includes human hands.

3. The method of claim 1 wherein the biosolvent mixture further comprises on a wt./wt. % basis 3 to 5% glycerol.

4. The method of claim 1 wherein the biosolvent mixture further contains a viscosifier.

5. The method of claim 4 wherein the viscosifier comprises a cellulose ester.

6. The method of claim 1 wherein the biosolvent mixture further contains from 1 to 2 wt. % of an organic acid.

7. The method of claim 1 wherein the lactate ester is ethyl lactate and the alcohol is ethanol.

8. The method of claim 1 wherein the biosolvent mixture comprises on a wt./wt. % basis 70 to 80% ethanol and 15 to 25% ethyl lactate.

9. The method of claim 1 wherein the biosolvent mixture provides bactericidal activity that kills at least 99.99% of the bacterial contamination from the human skin.

10. The method of claim 1 wherein the biosolvent mixture further comprises on a (wt./wt.) basis a total of 1% to 5% of at least one of Vitamin E and a fragrance.

11. The method of claim 1 wherein only intrinsic water from the hand is present when contacting the human skin with the biosolvent mixture.

12. The method of claim 1 wherein only intrinsic water is present when contacting the human skin with the biosolvent mixture.

* * * * *